United States Patent
Jeong et al.

(10) Patent No.: US 9,149,256 B2
(45) Date of Patent: Oct. 6, 2015

(54) ULTRASOUND STRAIN IMAGING BASED ON LATERAL DISPLACEMENT COMPENSATION

(75) Inventors: Mok Kun Jeong, Seoul (KR); Sung Jae Kwon, Seoul (KR); Dong Kuk Shin, Seoul (KR)

(73) Assignee: SAMSUNG MEDISON CO., LTD., Hongchun-Gun, Kangwon-Do (KR)

( * ) Notice: Subject to any disclaimer, the term of this patent is extended or adjusted under 35 U.S.C. 154(b) by 405 days.

(21) Appl. No.: 13/152,832

(22) Filed: Jun. 3, 2011

(65) Prior Publication Data

US 2012/0065505 A1  Mar. 15, 2012

(30) Foreign Application Priority Data

Sep. 15, 2010 (KR) .................. 10-2010-0090655

(51) Int. Cl.
*A61B 8/08* (2006.01)
(52) U.S. Cl.
CPC ...................... *A61B 8/485* (2013.01)
(58) Field of Classification Search
USPC ........................................ 600/407, 437–457
See application file for complete search history.

(56) References Cited

U.S. PATENT DOCUMENTS

| 6,508,768 | B1 * | 1/2003 | Hall et al. .................. 600/443 |
| 2003/0083578 | A1 * | 5/2003 | Abe et al. .................. 600/447 |
| 2007/0038090 | A1 | 2/2007 | Moon et al. |
| 2007/0197915 | A1 | 8/2007 | Jeong et al. |
| 2008/0275340 | A1 * | 11/2008 | Beach et al. ................. 600/438 |
| 2008/0287792 | A1 * | 11/2008 | Bae et al. .................. 600/438 |
| 2009/0105589 | A1 | 4/2009 | Osaka et al. |
| 2009/0182234 | A1 * | 7/2009 | Perrey et al. ................ 600/443 |

FOREIGN PATENT DOCUMENTS

| KR | 10-2007-0013986 | 1/2007 |
| KR | 10-2007-0077538 A | 7/2007 |

OTHER PUBLICATIONS

Korean Office Action issued in Korean Patent Application No. KR 10-2010-0090655 dated Oct. 7, 2011.
Korean Office Action issued in Korean Patent Application No. KR 10-2010-0090655 dated Feb. 7, 2012.

\* cited by examiner

*Primary Examiner* — Mark Remaly
(74) *Attorney, Agent, or Firm* — McDermott Will & Emery LLP

(57) ABSTRACT

Embodiments for forming a strain image by compensating for displacement in a later direction in an ultrasound system are disclosed. In one embodiment, an ultrasound system includes: an ultrasound data acquisition unit configured to acquire first ultrasound data where compression is not applied to a target object and second ultrasound data where compression is applied to the target object; and a processing unit configured to compensate for displacements in axial and lateral directions in the second ultrasound data based on the first ultrasound data and second ultrasound data, the processing unit being further configured to form a strain image based on the first ultrasound data and the axial and lateral displacement compensated second ultrasound data.

12 Claims, 7 Drawing Sheets

ULTRASOUND STRAIN IMAGING BASED ON LATERAL DISPLACEMENT COMPENSATION

CROSS-REFERENCE TO RELATED APPLICATIONS

The present application claims priority from Korean Patent Application No. 10-2010-0090655 filed on Sep. 15, 2010, the entire subject matter of which is incorporated herein by reference.

TECHNICAL FIELD

The present disclosure generally relates to ultrasound strain imaging, and more particularly to ultrasound strain imaging based on lateral displacement compensation in an ultrasound system.

BACKGROUND

An ultrasound system has become an important and popular diagnostic tool since it has a wide range of applications. Specifically, due to its non-invasive and non-destructive nature, the ultrasound system has been extensively used in the medical profession. Modern high-performance ultrasound systems and techniques are commonly used to produce two or three-dimensional images of internal features of an object (e.g., human organs).

Generally, the ultrasound image is displayed in a Brightness-mode (B-mode) by using reflectivity caused by an acoustic impedance difference between the tissues of the target object. However, if the reflectivity of the target object is hardly different from those of the neighboring tissues such as tumor, cancer or the like, then it is not easy to recognize the target object in the B-mode image.

To cope with the problem of recognizing the tumor, cancer and the like in the B-mode, an ultrasound elasticity imaging has been developed to visualize the mechanical characteristics of the tissues based on differences responsive to pre-compression and post-compression. Such imaging proved very helpful for diagnosing lesions such as tumor and cancer, which otherwise are hardly recognized in the B-mode image, in soft tissues (e.g., breast). The ultrasound elasticity imaging may utilize the scientific property that the elasticity of the tissues is related to a pathological phenomenon. For example, the tumor or cancer is relatively stiffer than the surrounding normal tissues. Thus, when stress is uniformly applied, a strain of the tumor or cancer may be typically smaller than those of the surrounding tissues. Strain refers to deformation of a target object due to stress applied per area and Young's modulus may be defined as a ratio of stress over strain.

Generally, if the stress is applied to a target object, then tissues in the target object may be compressed in an axial direction and moved out in a lateral direction. The conventional ultrasound elasticity imaging may use only the displacements in an axial direction to form a strain image without considering the movement in a lateral direction. Thus, there is a problem that an accurate strain image may not be formed due to a calculation error of the displacements.

SUMMARY

Embodiments for ultrasound strain imaging based on lateral displacement compensation in an ultrasound system are disclosed herein. In one embodiment, by way of non-limiting example, an ultrasound system comprises: an ultrasound data acquisition unit configured to acquire first ultrasound data where compression is not applied to a target object and second ultrasound data where compression is applied to the target object; and a processing unit configured to compensate for displacements in axial and lateral directions in the second ultrasound data based on the first ultrasound data and second ultrasound data, the processing unit being further configured to form a strain image based on the first ultrasound data and the axial and lateral displacement compensated second ultrasound data.

In another embodiment, a method of forming a strain image in an ultrasound system, comprises: a) acquiring first ultrasound data where compression is not applied to a target object; b) acquiring second ultrasound data where compression is applied to the target object; c) compensating for displacements in axial and lateral directions in the second ultrasound data based on the first ultrasound data and second ultrasound data; and d) forming a strain image based on the first ultrasound data and the axial and lateral displacement compensated second ultrasound data.

In another embodiment, a computer-readable storage medium storing instructions that, when executed by a computer, cause the computer to perform a method of forming a strain image, is provided. The method comprises: a) acquiring first ultrasound data where compression is not applied to a target object; b) acquiring second ultrasound data where compression is applied to the target object; c) compensating for displacements in axial and lateral directions in the second ultrasound data based on the first ultrasound data and second ultrasound data; and d) forming a strain image based on the first ultrasound data and the axial and lateral displacement compensated second ultrasound data.

The Summary is provided to introduce a selection of concepts in a simplified form that are further described below in the Detailed Description. This Summary is not intended to identify key or essential features of the claimed subject matter, nor is it intended to be used in determining the scope of the claimed subject matter.

DETAILED DESCRIPTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

Figure 1:
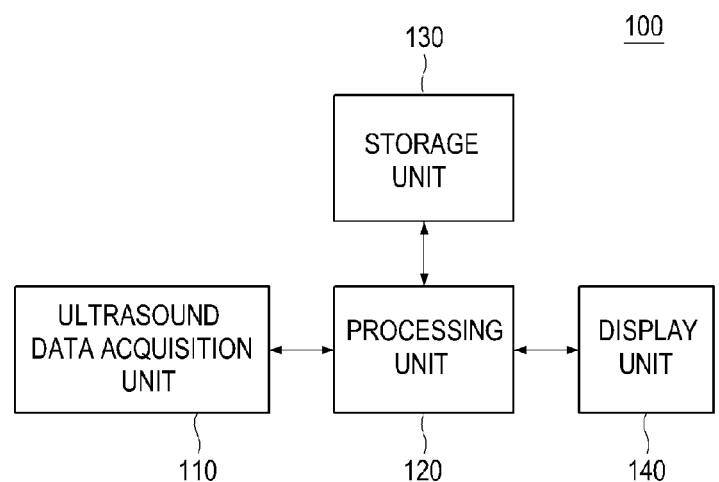
FIG. 1 is a block diagram showing an illustrative embodiment of an ultrasound system.

Referring to FIG. 1, an ultrasound system constructed in accordance with one embodiment is shown. The ultrasound system 100 may include an ultrasound data acquisition unit 110, a processing unit 120, a storage unit 130 and a display unit 140.

The ultrasound data acquisition unit 110 may be configured to transmit ultrasound beams to a target object and receive ultrasound echoes reflected from the target object to thereby form ultrasound data representative of the target object. An operation of the ultrasound acquisition unit will be described in detail by referring to FIG. 2.

Figure 2:
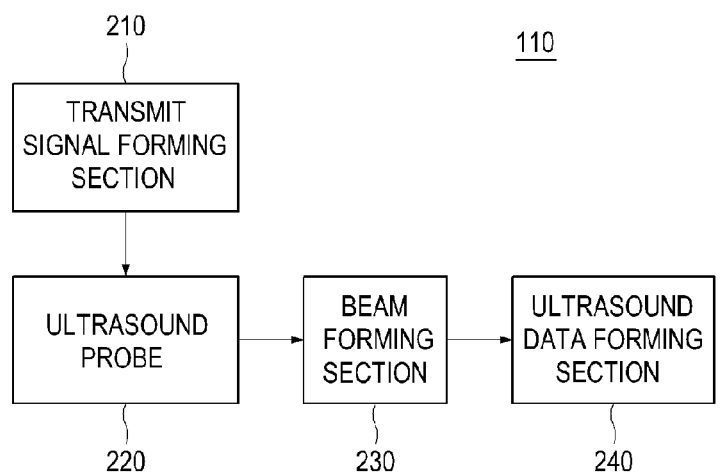
FIG. 2 is a block diagram showing an illustrative embodiment of an ultrasound data acquisition unit of FIG. 1.

FIG. 2 is a block diagram showing an illustrative embodiment of the ultrasound data acquisition unit 110. Referring to FIG. 2, the ultrasound data acquisition unit 110 may include a transmit signal forming section 210. The transmit signal forming section 210 may generate a plurality of transmit signals and apply delays to the transmit signals.

Figure 3:
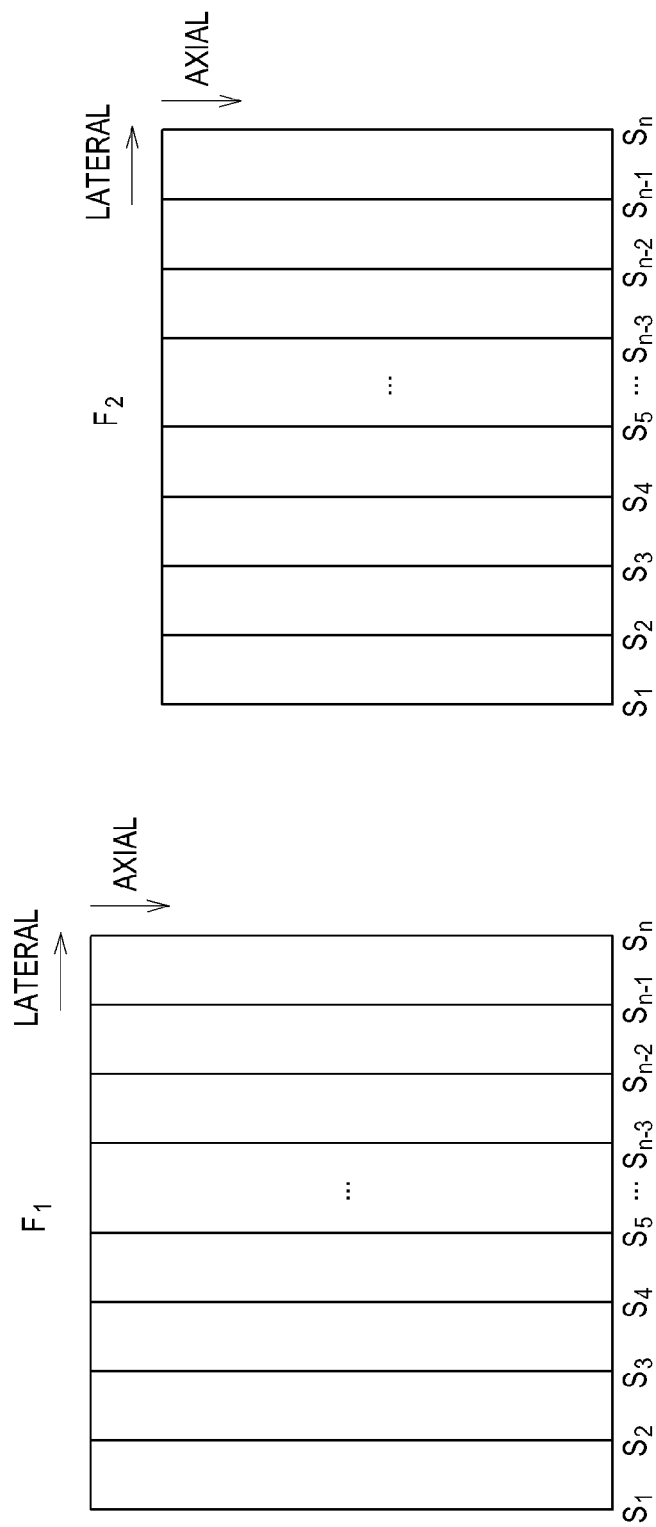
FIG. 3 is a schematic diagram showing frames of pre-compression and post-compression.

The ultrasound data acquisition unit 110 may further include an ultrasound probe 220, which is coupled to the transmit signal forming section 210. The ultrasound probe 220 may include an array transducer containing a plurality of transducer elements for reciprocal conversion between electric signals and ultrasound signals. The ultrasound probe 220 may be configured to transmit ultrasound signals in response to the transmit signals. The ultrasound probe 220 may be further configured to receive ultrasound echoes reflected from the target object to thereby output receive signals. As shown in FIG. 3, the receive signals may include first receive signals corresponding to a plurality scan lines $S_1$ to $S_N$, which are obtained without applying compression to the target object, and second receive signals corresponding to a plurality scan lines $S_1$ to $S_N$, which are obtained with applying compression to the target object, wherein N is an integer greater than 1. The compression may be applied by using the ultrasound probe 220. In such a case, a compression plate may be mounted around a front side of the ultrasound probe 220. In another embodiment, an additional device for compressing the target object may be employed.

The ultrasound data acquisition unit 110 may further include a beam forming section 230, which is coupled to the ultrasound probe 220. The beam forming section 230 may be configured to digitize the electrical receive signals into digital signals. The beam forming section 230 may also apply delays to the digital signals in consideration of distances between the elements of the ultrasound probe 220 and focal points. The beam forming section 230 may further sum the delayed digital signals to form receive-focused signals. In one embodiment, the beam forming section 230 may form first receive-focused signals based on the first receive signals and second receive-focused signals based on the second receive signals.

The ultrasound data acquisition unit 110 may further include an ultrasound data forming section 240, which is coupled to the beam forming section 230. The ultrasound data forming section 240 may be configured to form ultrasound data corresponding to a plurality of frames based on the receive-focused signals. The ultrasound data may include RF data sets or in-phase/quadrature (IQ) data sets. However, the ultrasound data may not be limited thereto. The ultrasound data forming section 240 may be further configured to perform a variety of signal processing (e.g., gain adjustment, filtering, etc.) upon the receive-focused signals. In one embodiment, the ultrasound data may include a first ultrasound data corresponding to scan lines $S_i$, which are formed based on the first receive-focused signals, and a second ultrasound data corresponding to scan lines $S_i$ that are formed based on the second receive-focused signals, wherein $1 \le I \le N$.

Referring back to FIG. 1, the processing unit 120, which is coupled to the ultrasound data acquisition unit 110, may be embodied with at least one of a central processing unit, a microprocessor, a graphic processing unit and the like. However, the processing unit 120 may not be limited thereto.

Figure 4:
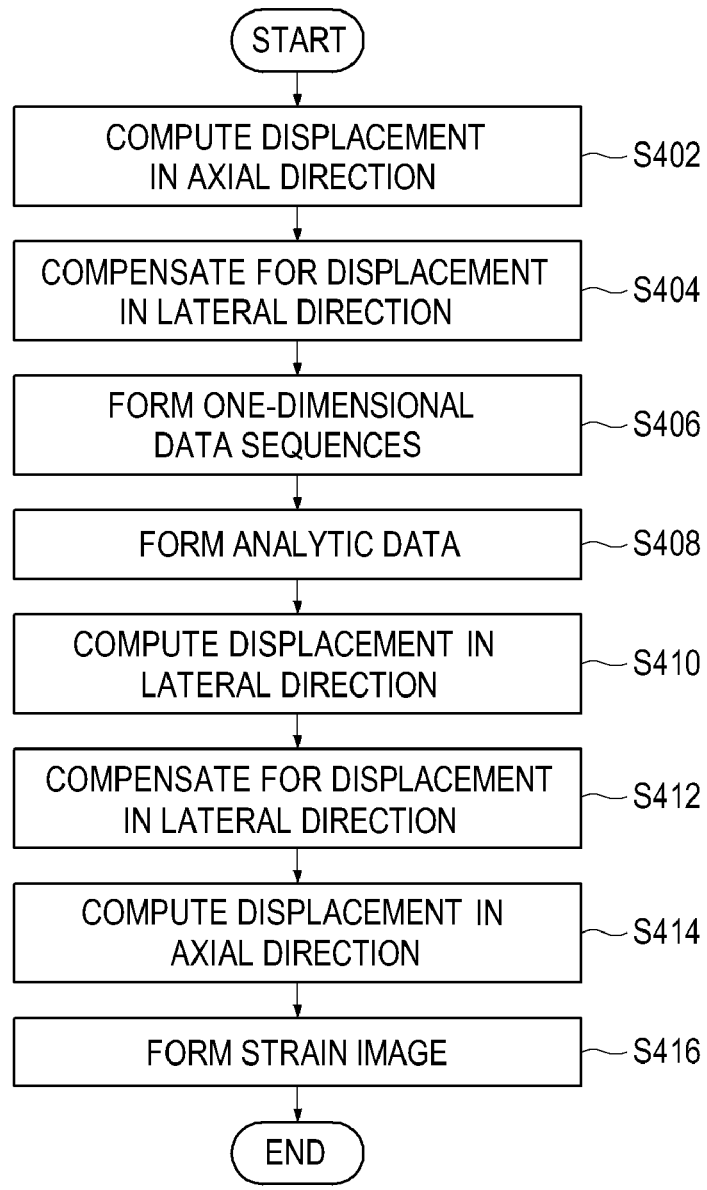
FIG. 4 is a flowchart showing an illustrative embodiment of forming a strain image.

FIG. 4 is a flowchart showing an illustrative embodiment of forming the strain image. Referring to FIG. 4, the processing unit 120 may be configured to compute displacement in an axial direction by using the first and second ultrasound data, which are provided from the ultrasound data acquisition unit 110, at S402.

Figure 5:
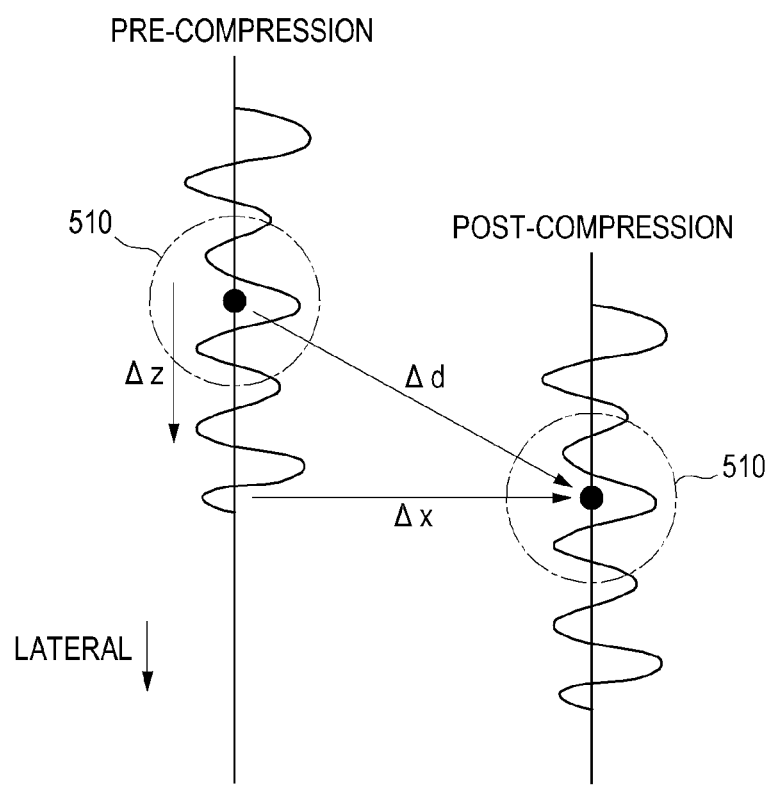
FIG. 5 is a schematic diagram showing an example of medium movement in a target object due to compression applied thereto.

FIG. 5 is a schematic diagram showing an example of medium movement in a target object due to compression applied thereto. As shown in FIG. 5, when the target object is compressed by applying the stress, a medium 510 may be moved by Δz in an axial direction and Δx in a lateral direction. That is, the medium 510 may be two-dimensionally moved by Δd.

The ultrasound data obtained without applying compression to the target object, i.e., the first ultrasound data, and the ultrasound data obtained with applying compression to the target object, i.e., the second ultrasound data, are defined by the following equations for modeling the compression of medium within the target object.

$$S_{pre}(z,x) = r(z,x)$$
$$S_{post}(z,x) = r(z-\Delta z, x-\Delta x) \quad (1)$$

wherein $S_{pre}(z, x)$ represents the first ultrasound data, $S_{post}(z, x)$ represents the second ultrasound data, $r(z, x)$ and $r(z-\Delta z, x-\Delta x)$ represent envelopes of the first and second data.

As indicated in Equation (1), the displacement of the lateral direction should be accurately computed in addition to the displacement of the axial direction. That is, the data moved by Δd should be accurately computed to compute an accurate displacement. When computing the displacement of the axial direction without considering the displacement of the lateral direction, a displacement Δz' of the axial direction including an error is merely computed.

The processing unit 120 may be configured to approximately compensate for the displacement of the axial direction in the post-compression ultrasound data, i.e., the second ultrasound data, based on the displacement Δz' of the axial direction including an error, at S404. In one embodiment, the processing unit 120 may be configured to apply the displacement Δz' of the axial direction including an error to Equation (1) to thereby compensate for the displacement Δz of the axial direction, as the following equation (2).

$$S_{pre}(z,x) = r(z,x)$$
$$S_{post}(z+\Delta z', x) = r(z+\Delta z', x-\Delta x) \quad (2)$$

Figure 6:
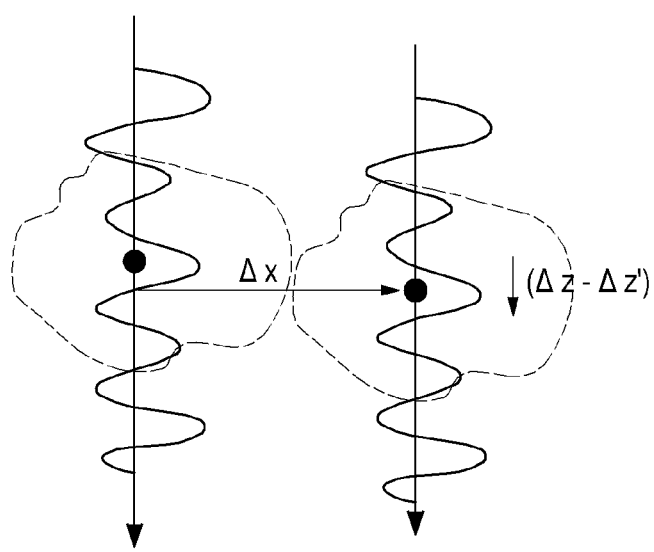
FIG. 6 is a schematic diagram showing an example of ultrasound data of post-compression in which displacements in a lateral direction are approximately compensated.

In Equation (2), assuming that Δz'≈Δz, the displacement of the lateral displacement is merely remained. FIG. 6 is a schematic diagram showing an example of ultrasound data of post-compression in which displacements in a lateral direction are approximately compensated.

Figure 7:
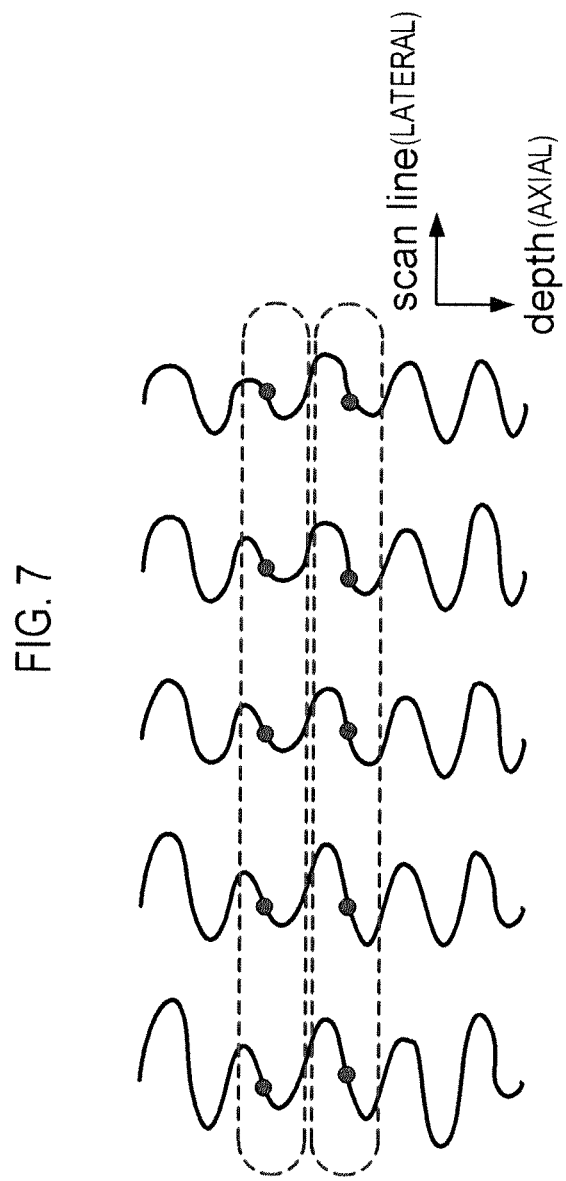
FIG. 7 is a schematic diagram showing an example of forming a one-dimensional data sequence in a lateral direction.

The processing unit 120 may be configured to form a one-dimensional data sequence in a lateral direction for the second ultrasound data whose displacement of the axial direction has been approximately compensated, as shown in FIG. 7, and to form one-dimensional data sequence in a lateral direction for the first ultrasound data, at S406. The one-dimensional data sequence may be formed by various well-known methods. Thus, detailed description thereof will be omitted herein.

The processing unit is configured to perform Hilbert transform upon the one-dimensional data sequence corresponding to the first ultrasound data and the one-dimensional data sequence corresponding to the second ultrasound data to form first analytic data corresponding to the first ultrasound data and second analytic data corresponding to the second ultrasound data, as S408. In one embodiment, the first analytic data and the second analytic data are complex data.

Figure 8:
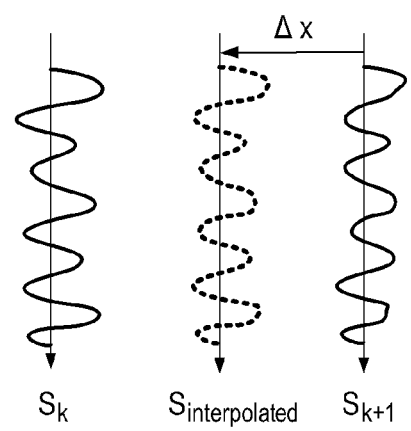
FIG. 8 is a schematic diagram showing an example of post-compression ultrasound data in which displacement in a lateral direction are compensated.

The processing unit 120 may be configured to compute the displacement Δx of the lateral direction by using a phase between the first analytic data and the second analytic data, at S410. The processing unit 120 may be configured to compensate for the displacement of the lateral direction in the second ultrasound data based on the computed Δx of the lateral direction, at S412. In one embodiment, the processing unit 120 may be configured to form interpolation data for compensating movement in a lateral direction by using the computed Δx of the lateral direction, as shown in FIG. 8. For example, the processing unit 120 may be configured to determine two scan lines $S_k$ and $S_{k+1}$ from scan lines of the second ultrasound data based on the computed Δx of the lateral direction, as shown in FIG. 8. The processing unit 120 may be configured to interpolate ultrasound data corresponding to the determined two scan lines from $S_k$ and $S_{k+1}$ from the second ultrasound data in which the displacement of the axial direction is approximately compensated, thereby forming interpolation data corresponding to an interpolation scan line $S_{interpolation}$.

The processing unit 120 may be configured to perform auto-correlation upon the first ultrasound data and the interpolation data to compute a displacement in an axial direction, at 5414. The processing unit 120 may be configured to form the strain image by using the computed displacement of the axial direction, at 5416.

Referring to FIG. 1, the storage unit 130, which is coupled to the ultrasound data acquisition unit 110 via the processing unit 120, is configured to store the ultrasound data acquired in the ultrasound data acquisition unit 110. Also, the storage unit 130 may be configured to store the computed displacements. The display unit 140 may display the strain image, which has been formed in the processing unit 120. The display unit 140 may include at least one of a cathode ray tube (CRT) display, a liquid crystal display (LCD), an organic light emitting diode (OLED) display and the like.

In another embodiment, a computer-readable storage medium storing instructions that, when executed by a computer, cause the computer to perform a method of forming a strain image, is provided. The method comprises: acquiring first ultrasound data where compression is not applied to a target object; acquiring second ultrasound data where compression is applied to the target object; compensating for displacements in axial and lateral directions in the second ultrasound data based on the first ultrasound data and second ultrasound data; and forming a strain image based on the first ultrasound data and the axial and lateral displacement compensated second ultrasound data.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound system, comprising:
   an ultrasound data acquisition unit configured to acquire first ultrasound data where a target object is in a first state of compression and second ultrasound data where the target object is in a second state of compression; and
   a processor configured to compute an axial displacement between the first ultrasound data and the second ultrasound data in an axial direction and a lateral displacement between the first ultrasound data and the second ultrasound data in a lateral direction, and compensate the second ultrasound data by using the computed axial displacement and the lateral displacement in the axial direction and the lateral direction, the processor being further configured to compute displacements between the first ultrasound data and the compensated second ultrasound data to form a strain image.

2. The ultrasound system of claim 1, wherein the processor is configured to:
   extract data in a lateral direction from the first ultrasound data to form a first one-dimensional data sequence,
   compensate the second ultrasound data by using the axial displacement to form intermediate second ultrasound data and extract data in a lateral direction from the intermediate second ultrasound data to form a second one-dimensional data sequence,
   perform Hilbert transform upon the first one-dimensional data sequence and the second one-dimensional data sequence to form first analytic data and second analytic data, respectively, and
   compute displacements between the first analytic data and the second analytic data.

3. The ultrasound system of claim 2, wherein the first analytic data and the second analytic data include complex data.

4. The ultrasound system of claim 2, wherein the processor is configured to interpolate ultrasound data corresponding to two scan lines from the intermediate second ultrasound data by using the displacements of the lateral direction to form interpolation data.

5. The ultrasound system of claim 4, wherein the processor is configured to perform an auto-correlation upon the first ultrasound data and the interpolation data to compute the displacements of the axial direction, and form the strain image by using the computed displacements of the axial direction.

6. The ultrasound system of claim 1, wherein the ultrasound data acquisition unit includes an ultrasound probe.

7. A method of forming a strain image in an ultrasound system, comprising:
   a) acquiring first ultrasound data where a target object is in a first state of compression;
   b) acquiring second ultrasound data where the target object is in a second state of compression;
   c) computing an axial displacement between the first ultrasound data and the second ultrasound data in axial direction and a lateral displacement between the first ultrasound data and the second ultrasound data in lateral direction, and compensating the second ultrasound data by using the computer axial displacement and the lateral displacement in the axial direction and the lateral direction; and
   d) computing displacements between the first ultrasound data and the compensated second ultrasound data to form a strain image.

8. The method of claim 7 wherein the includes:

extracting data in a lateral direction from the first ultrasound data to form a first one-dimensional data sequence;

performing Hilbert transform upon the first one-dimensional data sequence to form first analytic data;

compensating the second ultrasound data by using the axial displacement to form intermediate second ultrasound data and extracting data in a lateral direction from the intermediate second ultrasound data to form a second one-dimensional data sequence;

performing Hilbert transform upon the second one-dimensional data sequence to form second analytic data; and computing the displacements between the first analytic data and the second analytic data.

9. The method of claim 8, wherein the first analytic data and the second analytic data include complex data.

10. The method of claim 8, wherein the step c4) includes:

interpolating ultrasound data corresponding to neighboring two scan lines from the second ultrasound data whose axial displacements are compensated by using the displacements of the lateral direction to form interpolation data.

11. The method of claim 10, wherein the step d) includes:

performing auto-correlation upon the first ultrasound data and the interpolation data to compute the displacement of the axial direction; and forming the strain image by using the computed displacements of the axial direction.

12. A non-transitory computer-readable storage medium storing instructions that, when executed by a computer, cause the computer to perform a method of forming a strain image, the method comprising:

a) acquiring first ultrasound data where a target object is in a first state of compression;

b) acquiring second ultrasound data where the target object is in a second state of compression;

c) computing an axial displacement between the first ultrasound data and the second ultrasound data in axial direction and a lateral displacement between the first ultrasound data and the second ultrasound data in lateral direction, and compensating the second ultrasound data by using the computer axial displacement and the lateral displacement in the axial direction and the lateral direction; and d) computing displacements between the first ultrasound data and the compensated second ultrasound data to form a strain image.

* * * * *